(12) United States Patent
Yang et al.

(10) Patent No.: US 9,482,696 B2
(45) Date of Patent: Nov. 1, 2016

(54) METHOD AND DEVICE FOR MEASURING CURRENT

(71) Applicant: Huawei Administration Building, Shenzhen (CN)

(72) Inventors: Jing Yang, Shenzhen (CN); Qinghuan Wei, Shenzhen (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 398 days.

(21) Appl. No.: 14/099,036

(22) Filed: Dec. 6, 2013

(65) Prior Publication Data

US 2014/0118013 A1 May 1, 2014

Related U.S. Application Data

(63) Continuation of application No. PCT/CN2013/073877, filed on Apr. 8, 2013.

(30) Foreign Application Priority Data

Oct. 31, 2012 (CN) .......................... 2012 1 0426192

(51) Int. Cl.
    *G03G 15/20* (2006.01)
    *G01R 1/20* (2006.01)
    *G01R 27/08* (2006.01)
    *G01N 27/02* (2006.01)
    *G01K 13/00* (2006.01)

(52) U.S. Cl.
CPC .............. *G01R 1/203* (2013.01); *G01K 13/00* (2013.01); *G01N 27/025* (2013.01); *G01R 27/08* (2013.01)

(58) Field of Classification Search
CPC .............................. G01N 27/025; G01R 27/08
USPC ........................................................... 324/713
See application file for complete search history.

(56) References Cited

U.S. PATENT DOCUMENTS

| | | | |
|---|---|---|---|
| 2001/0003419 A1 | 6/2001 | Ribes | |
| 2005/0127918 A1* | 6/2005 | Kutkut | G01R 31/3648 324/430 |
| 2009/0087725 A1* | 4/2009 | Sim | G01R 1/203 429/90 |

FOREIGN PATENT DOCUMENTS

| | | |
|---|---|---|
| CN | 101398446 A | 4/2009 |
| CN | 101650408 A | 2/2010 |
| CN | 102928657 A | 2/2013 |
| DE | 102004042719 A1 | 9/2005 |

* cited by examiner

*Primary Examiner* — Walter L Lindsay, Jr.
*Assistant Examiner* — Michael Harrison
(74) *Attorney, Agent, or Firm* — Brinks Gilson & Lione (57) ABSTRACT

A method and an electronic device are disclosed for measuring a current. The device measures a temperature between a first sampling point and a second sampling point on a metal structure carrying a current to be measured. The device outputs a first signal according to the measured temperature and a second signal after sampling and filtering the first signal. The device detects the first voltage signal at the first sampling point and the second voltage signal at the second sampling point. The device samples and filters a difference between the first voltage signal and the second voltage signal and outputs a third voltage signal. The device restores the second signal to a temperature value representing a temperature between the first sampling point and the second sampling point and calculates a resistance value between the first sampling point and the second sampling point according to the temperature value.

3 Claims, 5 Drawing Sheets

METHOD AND DEVICE FOR MEASURING CURRENT

CROSS-REFERENCE TO RELATED APPLICATIONS

This application is a continuation of International Application No. PCT/CN2013/073877, filed on Apr. 8, 2013, which claims priority to Chinese Patent Application No. 201210426192.3, filed on Oct. 31, 2012, both of which are hereby incorporated by reference in their entireties.

TECHNICAL FIELD

The present application relates to the field of electronic technologies, and in particular, to a method and a device for measuring a current.

BACKGROUND

A communication power supply is usually called the heart of a communication system. If the communication power supply works abnormally, a communication system fault may occur, and the whole system may even fail. Currently, a current diverter is used mostly to detect the current of a communication power supply.

When being used to perform sampling detection on the current, the current diverter is equivalent to a resistor with a small temperature drift coefficient. Therefore, it is obtained from the Ohm's law that, the voltage is proportional to the current, and the value of the current passing through the current diverter is calculated proportionally by obtaining the voltage values at both ends of the current diverter.

However, using the current diverter to perform sampling detection on the current has some inevitable defects. Because the current diverter has a large resistance value, when the current passing through the current diverter is 1000 A, a corresponding voltage drop of 75 MV is generated at the current diverter, and at this time, the power consumption of the current diverter is 75 W. Therefore, the power consumption of the current diverter is large. Because the large power consumption causes the temperature value of the current diverter to rise, and the resistance of the current diverter may change with the temperature, the stability of the current diverter is reduced. In addition, the cost of manufacturing the current diverter is relatively high.

SUMMARY

Embodiments of the present application disclose a method and a device for measuring a current, so as to reduce power consumption during the process of current sampling detection, and improve the stability of the current detection.

In a first aspect, an embodiment of the present application provides a method for measuring a current by an electronic device. The device measures a temperature between a first sampling point and a second sampling point on a metal bar carrying a current to be measured. The device outputs a first signal according to the measured temperature and a second signal after sampling and filtering the first signal. The device detects the first voltage signal at the first sampling point and the second voltage signal at the second sampling point. The device samples and filters a difference between the first voltage signal and the second voltage signal and outputs a third voltage signal. The device restores the second signal to a temperature value representing a temperature between the first sampling point and the second sampling point and calculates a resistance value between the first sampling point and the second sampling point according to the temperature value.

In second aspect, an embodiment of the present application provides a device for measuring a current. The device includes: a metal structure, a temperature sensor, a temperature sampling detector, a voltage sampling detector, an analog-digital converter, and a controller. The metal bar is configured to carry a current to be measured. The temperature sensor is configured to measure a temperature between a first sampling point and a second sampling point located on the metal structure, and output a first signal according to the measured temperature. The temperature sampling detector is configured to receive the first signal output by the temperature sensor, and output a second signal after sampling and filtering the first signal. The voltage sampling detector is configured to detect a first voltage signal at the first sampling point located on the metal structure and a second voltage signal at the second sampling point located on the metal structure, sample and filter a signal difference between the first voltage signal and the second voltage signal, and output a third voltage signal. The analog-digital converter, configured to: receive the second signal output by the temperature sampling detector, convert the second signal into a first digital signal, and output the first digital signal; and receive the third voltage signal output by the voltage sampling detector, convert the third voltage signal into a second digital signal, and output the second digital signal. The controller is configured to: receive the first digital signal and the second digital signal output by the analog-digital converter, restore, according to the first digital signal, the second signal to a temperature value representing a temperature between the first sampling point and the second sampling point, and calculate a resistance value between the first sampling point and the second sampling point according to the temperature value; and restore, according to the second digital signal, the third voltage signal to a voltage value representing a voltage between the first sampling point and the second sampling point, and calculate, according to the voltage value and the resistance value, the value of a current between the first sampling point and the second sampling point.

With the method and device for measuring a current provided by the embodiments of the present application, the temperature sensor measures the temperature at any point between the sampling points on the copper bar, the controller converts the signal output by the temperature sensor into the temperature value and the resistance value of the sampling points on the copper bar, and indirectly measures the value of a current passing through the sampling points by using the resistance value and the voltage value of the sampling points. Meanwhile, multiple holes or apertures are arranged on the copper bar, which indirectly increases the resistance of the copper bar and reduces current power consumption, so as to lower the temperature of the copper bar, thereby improving the stability of a measuring system.

BRIEF DESCRIPTION OF DRAWINGS

FIG. 4-A is a schematic diagram of integrating a first analog-digital converter externally according to an embodiment of the present application;

FIG. 4-B is a schematic diagram of integrating a second analog-digital converter externally according to an embodiment of the present application;

FIG. 4-C is a schematic diagram of measuring a current by using an integrated temperature sensor according to an embodiment of the present application;

FIG. 5-A is a schematic diagram according to an embodiment of the present application;

FIG. 5-B is a schematic diagram according to another embodiment of the present application;

FIG. 5-C is a schematic diagram according to still another embodiment of the present application.

DESCRIPTION OF EMBODIMENTS

To make the objectives, solutions, and advantages of the embodiments of the present application more clearly, the following further describes the embodiments of the present application with reference to the accompanying drawings.

Figure 1:
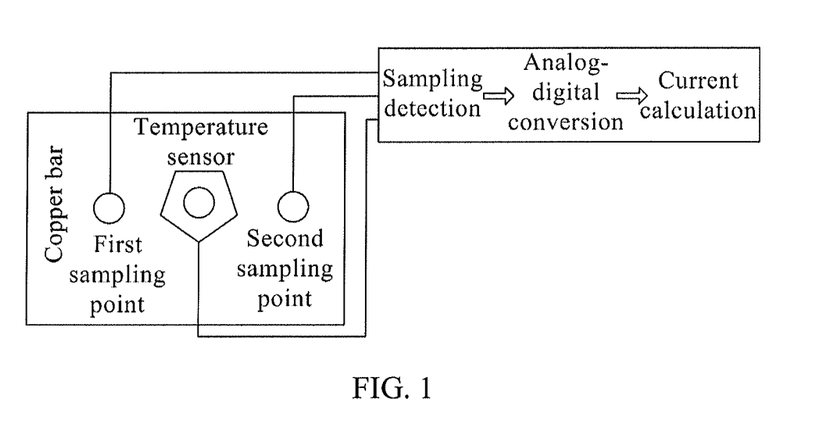
FIG. 1 is a structural diagram of measuring a current according to an embodiment of the present application.

The following takes FIG. 1 as an example to describe in detail the device for measuring a current provided in an embodiment of the present application. FIG. 1 is a structural diagram of measuring a current according to an embodiment of the present application.

As shown in FIG. 1, a temperature and a voltage between a first sampling point and a second sampling point are measured; the measured temperature between the first sampling point and the second sampling point undergoes sampling detection and analog-digital conversion, and then is converted into a resistance value between the first sampling point and the second sampling point; the measured voltage between the first sampling point and the second sampling point undergoes sampling detection and analog-digital conversion, and then is converted into a voltage value between the first sampling point and the second sampling point; and the value of a current between the first sampling point and the second sampling point on a copper bar is calculated by using the resistance value and the voltage value between the first sampling point and the second sampling point.

Figure 2:
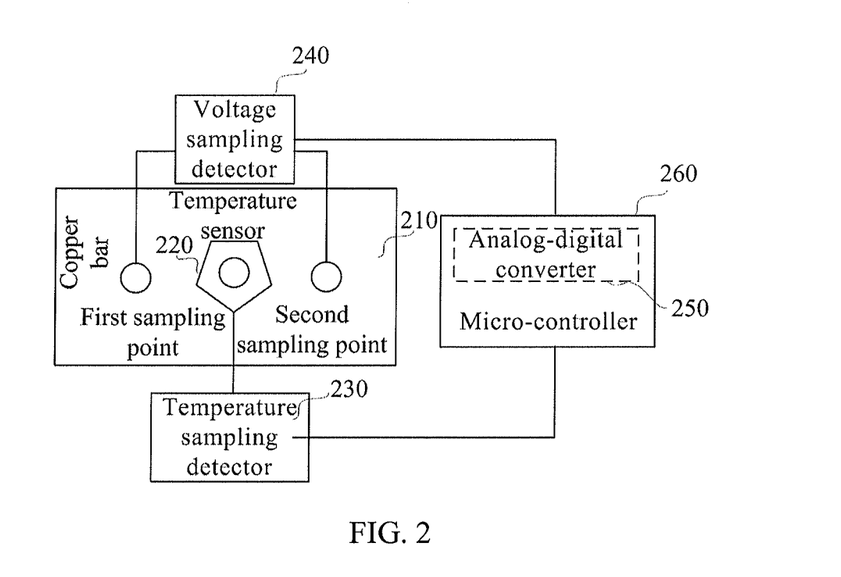
FIG. 2 is a diagram of a device for measuring a current according to an embodiment of the present application.

The following takes FIG. 2 as an example to describe in detail the device for measuring a current provided in an embodiment of the present application. FIG. 2 is a diagram of a device for measuring a current according to an embodiment of the present application.

As shown in FIG. 2, the device includes a metal structure 210, a temperature sensor 220, a temperature sampling detector 230, a voltage sampling detector 240, an analog-digital converter 250, and a controller 260. The metal structure may be a copper bar or other similar metal.

Two sampling points, that is, a first sampling point and a second sampling point, are selected on the copper bar 210. The two sampling points are secured by using a screw (or a buckle). The first sampling point and the second sampling point are connected to the voltage sampling detector 240. The temperature sensor 220 is placed between the two sampling points, and is also secured by using a screw (or a buckle). The temperature sensor 220 is connected to the temperature sampling detector 230. The temperature sampling detector 230 and the voltage sampling detector 240 are connected to the controller 260, where the analog-digital converter 250 may be integrated inside the controller 260; or the analog-digital converter is integrated outside the controller 260, that is, the analog-digital converter 250 is deployed separately. In this embodiment of the present application, integrating the analog-digital converter 250 inside the controller 260 is taken as an example.

The copper bar 210 in the device is configured to carry a current to be measured.

The temperature sensor 220 is configured to measure a temperature between the first sampling point and the second sampling point located on the copper bar, and output a first signal according to the measured temperature.

Specifically, the temperature sensor 220 is placed between the two sampling points, and is secured by using a screw (or a buckle). The temperature sensor 220 measures the temperature at any point between the two sampling points. After the copper bar is fed with a direct current or an alternating current, the temperature sensor 220 starts to operate, and measures the temperature at any point between the first sampling point and the second sampling point.

It should be understood that, the temperature sensor 220 has various types. In practical applications, other types of temperature sensors can be used, for example, an integrated temperature sensor which has an analog-digital conversion integrated inside and provides digital bus communication externally; a current-type temperature sensor, where the signal output by the sensor is a current signal which is converted into a voltage signal after being sampled and detected; a voltage-type temperature sensor, where the signal output by the sensor is a voltage signal. In addition, any type of temperature sensor may operate normally when a direct current or an alternating current passes through it. In the embodiment of the present application, a thermistor-type temperature sensor is taken as an example, and the temperature sensor outputs a voltage signal. The temperature sensor is a thermistor-type temperature sensor, and the temperature sensor outputs a voltage signal, where the voltage signal represents a temperature value at any point between the sampling points.

It should be noted that, the temperature sensor 220 is fed with an external power supply or an internal power supply.

The temperature sampling detector 230 is configured to receive the first signal output by the temperature sensor, and output a second signal after sampling and filtering the first signal.

Specifically, the temperature sampling detector 230 samples, filters, and proportionally scales the first signal, and outputs a second signal after the processing.

The voltage sampling detector 240 is configured to detect a first voltage signal at the first sampling point located on the copper bar and a second voltage signal at the second sampling point located on the copper bar, sample and filter a signal difference between the first voltage signal and the second voltage signal, and output a third voltage signal.

Specifically, the voltage sampling detector 240 is connected to the first sampling point and the second sampling point on the copper bar, and detects the first voltage signal at the first sampling point and the second voltage signal at the second sampling point, obtains the signal difference between the first voltage signal and the second voltage signal, samples, filters, and proportionally scales the signal difference of the sampling points, and outputs a third voltage signal after the processing.

It should be understood that, because selected temperature sensors 220 may be different in type, the first signals output by the temperature sensors 220 are different. When a temperature sensor 220 outputs a voltage signal, the content to be measured for the first signal or the first voltage signal or the second voltage signal is different. The first signal represents the temperature between the first sampling point and the second sampling point, and the first voltage signal and the second voltage signal represent voltages generated by the first sampling point and the second sampling point respectively when a current passes through.

The analog-digital converter 250 is configured to: receive the second signal output by the temperature sampling detector, convert the second signal into a first digital signal, and output the first digital signal; and receive the third voltage signal output by the voltage sampling detector, convert the third voltage signal into a second digital signal, and output the second digital signal.

The controller 260 is configured to: receive the first digital signal and the second digital signal output by the analog-digital converter, restore, according to the first digital signal, the second signal to a temperature value representing a temperature between the first sampling point and the second sampling point, and calculate a resistance value between the first sampling point and the second sampling point according to the temperature value; and restore, according to the second digital signal, the third voltage signal to a voltage value representing a voltage between the first sampling point and the second sampling point, and calculate, according to the voltage value and the resistance value, the value of a current between the first sampling point and the second sampling point.

Specifically, the controller 260 receives the first digital signal obtained after the processing performed by the analog-digital converter 250, restores the first digital signal to a temperature value representing a temperature between the first sampling point and the second sampling point. Then the controller 260 invokes a self-stored resistance-temperature comparison table or a resistance-temperature formula, and calculates the resistance value between the first sampling point and the second temperature value according to the temperature value.

The controller 260 further receives the second digital signal obtained after the processing performed by the analog-digital converter 250, and restores the second digital signal to a voltage value representing a voltage between the first sampling point and the second sampling point.

The controller 260 calculates the value of a current between the first sampling point and the second sampling point by using the voltage value and the resistance value.

Figure 3:
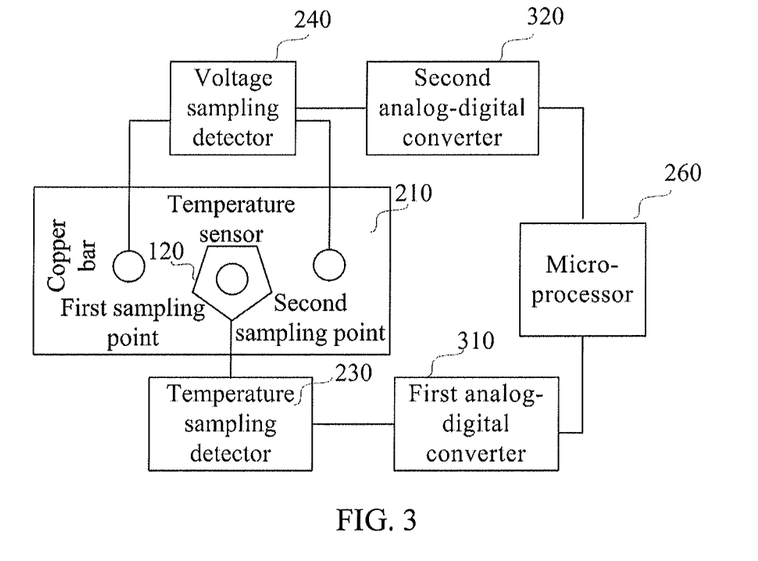
FIG. 3 is a schematic diagram of integrating analog-digital converters externally according to an embodiment of the present application.

In a preferred embodiment, as shown in FIG. 3, the analog-digital converter 250 is integrated outside the controller 260, that is, when the analog-digital converter 250 is deployed separately, the device may further include: a first analog-digital converter 310 and a second analog-digital converter 320. The first analog-digital converter 310 is connected to the temperature sampling detector 230, and is configured to receive the second signal, convert the second signal into a first digital signal, and transmit the first digital signal to the controller 260.

The second analog-digital converter 320 is connected to the voltage sampling detector 240, and is configured to receive the third voltage signal, convert the third voltage signal into a second digital signal, and transmit the second digital signal to the controller 260.

Figure 4:
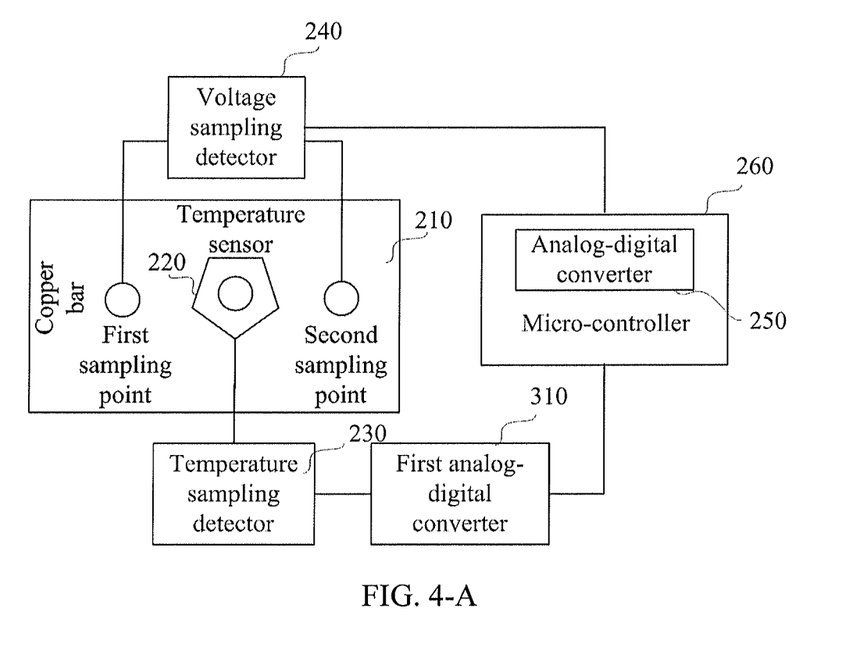

Further, in another preferred embodiment, if the analog-digital converter 250 is integrated inside the controller 260, meanwhile the first analog-digital converter 310 or second analog-digital converter 320 may be added to the device alternatively, so as to simplify the work load of the controller, improve the arithmetic speed of the controller, and enhance analog-digital conversion precision. As shown FIG. 4-A, the analog-digital converter 250 is integrated inside the controller 260, the first analog-digital converter 310 may be alternatively added. The first analog-digital converter 310 is connected to the temperature sampling detector 230, the first analog-digital converter 310 receives the second signal, converts the second signal into a first digital signal, and directly transmits the first digital signal to the controller 260. The controller 260 is further connected to the voltage sampling detector 240. The voltage sampling detector 240 directly transmits the third voltage signal to the controller 260; and the controller 260 converts the third voltage signal into a second digital signal by using the built-in integrated analog-digital converter 250, and converts the second digital signal into the voltage value between the sampling points.

As shown in FIG. 4-B, the analog-digital converter 250 is integrated inside the controller 260, and the second analog-digital converter 320 may be alternatively added. The second analog-digital converter 320 is connected to the voltage sampling detector 240; and the second analog-digital converter 320 receives the third voltage signal, converts the third voltage signal into a second digital signal, and directly transmits the second digital signal to the controller 260. The controller 260 is further connected to the temperature sampling detector 230. The temperature sampling detector 230 directly transmits the second signal to the controller 260. The controller 260 converts the second signal into a first digital signal by using the built-in integrated analog-digital converter 250, converts the first digital signal into the temperature value between the sampling points, and further calculates the resistance value between the sampling points.

It should be noted that, in the above embodiments, none of the temperature sensors 220 is an integrated temperature sensor. However, in practical applications, integrated temperature sensors may also be used. As shown in FIG. 4-C, FIG. 4-C shows another form of a device for measuring a current. When the temperature sensor 220 is an integrated temperature sensor, the temperature sampling detector 230 is replaced by a digital communication bus.

The integrated temperature sensor converts the measured temperature into a digital signal, and communicates with an on-chip peripheral bus corresponding to the controller 260 by using a digital bus interface such as I2C, onewire, SPI, or the like. The controller 260 reads, through the on-chip peripheral bus, the digital signal sampled by the integrated temperature sensor, and converts the digital signal into the temperature value between the first sampling point and the second sampling point.

It should be further noted that, the device further includes a power supply, which is not shown in the figure. The power supply loads a direct current or an alternating current for the copper bar 210. In the above embodiments, each component in the device for measuring a current is described by taking an example that the power supply loads a direct current. In practical applications, the power supply may also load an alternating current. When an alternating current is loaded, functions of the components in the device for measuring a current are the same, which are not described herein again. However, when the alternating current is loaded, in order to reduce the electrical interference of an alternating voltage on other components, the voltage sampling detector 240 and/or second analog-digital converter 320 should be isolated, to reduce the electrical interference of the two components on other components.

Figure 5:
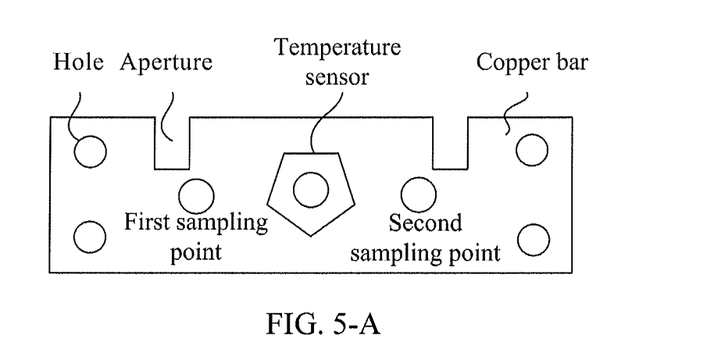

It should be further noted that, in order to reduce power consumption, and solve the problem of heat emission from the metal structure. The metal structure may include a copper bar 210, multiple holes and/or apertures may be further arranged on the copper bar 210 in the embodiment of the present application, to increase the resistance value of the copper bar 210, reduce the current passing through the copper bar 210, and indirectly reduce the power consumption. In addition, on the basis of retaining the heat dissipation area of the copper bar 210 between the sampling points, the sectional area of the copper bar 210 is decreased to reduce the heat emitted by the metal structure 210, as shown in FIG. 5-A, FIG. 5-B, and FIG. 5-C. However, the manner of decreasing the sectional area of the metal structure is not limited to the three types shown in FIG. 5-A, FIG. 5-B, and FIG. 5-C.

With the device for measuring a current provided by the embodiment of the present application, the temperature sensor measures the temperature at any point between the sampling points on the copper bar; the controller converts the signal output by the temperature sensor into the temperature value and the resistance value of the sampling points on the copper bar, and indirectly measures the value of the current passing through the sampling points by using the resistance value and the voltage value of the sampling points. Meanwhile, multiple holes or apertures are arranged on the copper bar, which indirectly increases the resistance of the copper bar and reduces current power consumption, so as to lower the temperature of the copper bar, thereby improving the stability of a measuring system.

Figure 6:
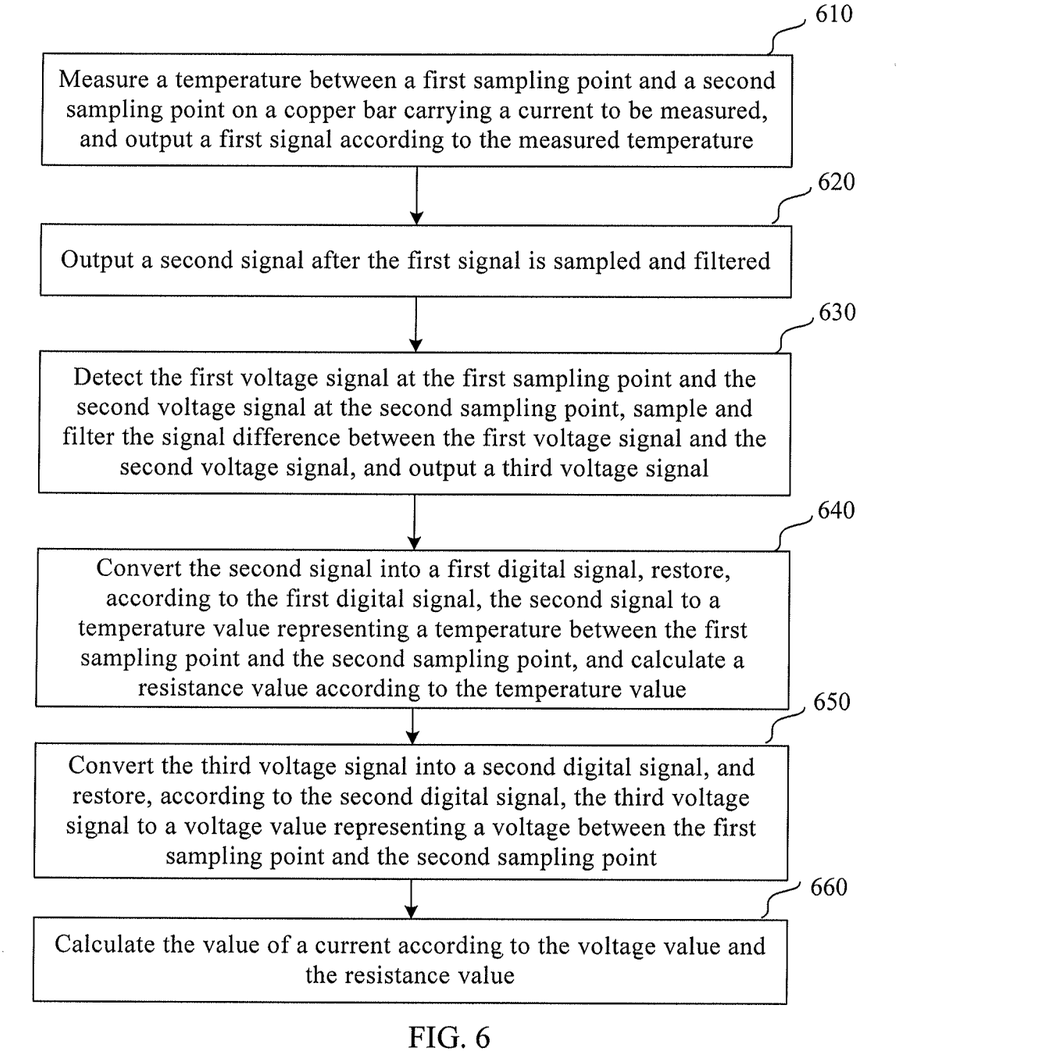
FIG. 6 is a flowchart of a method for measuring a current according to an embodiment of the present application.

The following takes FIG. 6 as an example to describe in detail a method for measuring a current provided in an embodiment of the present application. FIG. 6 is a flowchart of a method for measuring a current according to an embodiment of the present application.

The method shown in FIG. 6 is implemented based on the aforementioned device embodiment. Based on the device for measuring a current, the method for measuring a current specifically includes the following steps:

Step 610: Measure a temperature between a first sampling point and a second sampling point on a copper bar carrying a current to be measured, and output a first signal according to the measured temperature.

Specifically, two sampling points, that is, a first sampling point and a second sampling point, are selected on the copper bar. The two sampling points are secured by using a screw (or a buckle). After a direct current or an alternating current is provided, the temperature at any point between the two sampling points is measured. In this embodiment of the present application, the first signal is output according to the measured temperature. In this embodiment of the present application, after the copper bar is fed with a direct current or an alternating current, the current to be measured is carried on the copper bar.

Step 620: Output a second signal after the first signal is sampled and filtered.

Specifically, based on the description in step 610, the first signal is sampled, filtered, and proportionally scaled, and a second signal is output after the processing.

Step 630: Detect a first voltage signal at the first sampling point and a second voltage signal at the second sampling point, sample and filter a signal difference between the first voltage signal and the second voltage signal, and output a third voltage signal.

Specifically, because the copper bar is fed with a direct current or an alternating current, voltages appears at the first sampling point and the second sampling point on the copper bar. The first voltage signal at the first sampling point and the second voltage signal at the second sampling point are detected, the signal difference between the first voltage signal and the second voltage signal is obtained, the signal difference is sampled, filtered, and proportionally scaled, and a third voltage signal is output after the processing.

Step 640: Convert the second signal into a first digital signal, restore, according to the first digital signal, the second signal to a temperature value representing a temperature between the first sampling point and the second sampling point, and calculate a resistance value between the first sampling point and the second sampling point according to the temperature value.

Specifically, based on the description in the above steps, the second signal is converted into the first digital signal, and the first digital signal is converted into the value representing a temperature between the first sampling point and the second sampling point, a resistance-temperature comparison table or a resistance-temperature formula is invoked, and the resistance value between the first sampling point and the second sampling point at the temperature value is calculated.

Step 650: Convert the third voltage signal into a second digital signal, and restore, according to the second digital signal, the third voltage signal to a voltage value representing a voltage between the first sampling point and the second sampling point.

Specifically, based on the description in the above steps, the third voltage signal is converted into a second digital signal, and the second digital signal is converted into the voltage value representing the voltage between the first sampling point and the second sampling point.

Step 660: Calculate, according to the voltage value and the resistance value, the value of a current between the first sampling point and the second sampling point.

Specifically, the value of the current between the first sampling point and the second sampling point is calculated according to the resistance value obtained in step 640 and the voltage value obtained in step 650 by using the Ohm's law.

It should be further noted that, in order to reduce power consumption, and solve the problem of heat emission from the copper bar, multiple holes and/or apertures may be further arranged on the copper bar in the embodiments of the present application, to increase the resistance value of the copper bar, reduce the current passing through the copper bar, and indirectly reduce the power consumption. In addition, on the basis of retaining the heat dissipation area of the copper bar between the sampling points, the sectional area of the copper bar is decreased to reduce the heat emitted by the copper bar, as shown in FIG. 5-A, FIG. 5-B, and FIG. 5-C. However, the manner of decreasing the sectional area of the copper bar is not limited to the three types shown in FIG. 5-A, FIG. 5-B, and FIG. 5-C.

With the method for measuring a current provided by the embodiment of the present application, the temperature at any point between the sampling points on the copper bar is measured; the signal representing the temperature is converted into the temperature value and the resistance value of the sampling points on the copper bar; and the value of the current passing through the sampling points is calculated indirectly by using the resistance value and the voltage value of the sampling points. Meanwhile, multiple holes or apertures are arranged on the copper bar, which indirectly increases the resistance of the copper bar, so as to lower the temperature of the copper bar, thereby improving the stability of a measuring system.

Those skilled in the art may further realize that, the components and steps described in the embodiments of the present application may be implemented by using electronic hardware, computer software, or a combination thereof; and in order to clearly describe the interchangeability between hardware and software, the above specification describes combinations and steps of various embodiments generally according to functions. Whether the functions are performed by hardware or software depends on particular applications and design constraint conditions of the solutions. Those skilled in the art may use different methods for each specific application to implement the described functions; however, this implementation shall not be deemed as going beyond the scope of the present application.

The objectives, solutions, and benefits of the present application are further described in detail in the foregoing specific embodiments. It should be understood that the foregoing description is merely about the specific embodiments of the present application, but is not intended to limit the protection scope of the present application. Any modification, equivalent replacement, or improvement made within the idea and principle of the present application shall fall within the protection scope of the present application.

What is claimed is:

1. An electronic device, comprising:
    a metal bar, configured to carry a current to be measured;
    a temperature sensor, configured to measure a temperature between a first sampling point and a second sampling point located on the metal structure, and output a first signal according to the measured temperature;
    a temperature sampling detector, configured to receive the first signal output by the temperature sensor, and output a second signal after sampling and filtering the first signal;
    a voltage sampling detector, configured to detect a first voltage signal at the first sampling point located on the metal structure and a second voltage signal at the second sampling point located on the metal structure, sample and filter a signal difference between the first voltage signal and the second voltage signal, and output a third voltage signal;
    an analog-digital converter, configured to: receive the second signal output by the temperature sampling detector, convert the second signal into a first digital signal, and output the first digital signal; and receive the third voltage signal output by the voltage sampling detector, convert the third voltage signal into a second digital signal, and output the second digital signal;
    a controller, configured to: receive the first digital signal and the second digital signal output by the analog-digital converter, restore, according to the first digital signal, the second signal to a temperature value representing the temperature between the first sampling point and the second sampling point, and calculate a resistance value between the first sampling point and the second sampling point according to the temperature value; and restore the third voltage signal to a voltage value representing a voltage between the first sampling point and the second sampling point according to the second digital signal, and calculate, according to the voltage value and the resistance value, a value of a current between the first sampling point and the second sampling point; and
    wherein the temperature sensor is placed on a midpoint between the two sampling points, and the two sampling points and the temperature sensor are surrounded by multiple holes defined in the metal bar and multiple notches depressed from lateral sides of the metal bar.

2. The electronic device according to claim 1, wherein the controller is specifically configured to:
    calculate the resistance value between the first sampling point and the second sampling point and corresponding to the temperature value by using a resistance-temperature comparison table or a resistance-temperature formula.

3. The device according to claim 1, wherein the analog-digital converter is integrated inside the controller; or the analog-digital converter is integrated outside the controller.

* * * * *

UNITED STATES PATENT AND TRADEMARK OFFICE
CERTIFICATE OF CORRECTION

PATENT NO. : 9,482,696 B2  
APPLICATION NO. : 14/099036  
DATED : November 1, 2016  
INVENTOR(S) : Jing Yang et al.

Page 1 of 1

It is certified that error appears in the above-identified patent and that said Letters Patent is hereby corrected as shown below:

On the Title Page

Left Column, item (71), replace "Huawei Administration Building," with --Huawei Technologies Co., Ltd.,--.

Signed and Sealed this  
Twentieth Day of August, 2019

Andrei Iancu  
*Director of the United States Patent and Trademark Office*